(12) United States Patent
Hartwick (10) Patent No.: US 7,670,351 B2
(45) Date of Patent: Mar. 2, 2010

(54) MEDICAL DEVICE USING BEAM CONSTRUCTION AND METHODS

(76) Inventor: Darrell Hartwick, 145 Washington St., Newton, MA (US) 02458

( * ) Notice: Subject to any disclaimer, the term of this patent is extended or adjusted under 35 U.S.C. 154(b) by 45 days.

(21) Appl. No.: 11/805,040

(22) Filed: May 21, 2007

(65) Prior Publication Data

US 2008/0004604 A1 Jan. 3, 2008

Related U.S. Application Data

(60) Provisional application No. 60/747,793, filed on May 20, 2006.

(51) Int. Cl.
*A61B 17/32* (2006.01)
(52) U.S. Cl. ...................................... 606/170
(58) Field of Classification Search ......... 606/139–148, 606/167–184, 205–210
See application file for complete search history.

(56) References Cited

U.S. PATENT DOCUMENTS

| | | | |
|---|---|---|---|
| 4,674,501 A * | 6/1987 | Greenberg | ................... 606/174 |
| 4,887,612 A | 12/1989 | Esser et al. | |
| 5,125,896 A | 6/1992 | Hojeibane | |
| 5,358,478 A | 10/1994 | Thompson et al. | |
| 5,394,885 A | 3/1995 | Francese | |
| 5,395,329 A | 3/1995 | Fleischhacker et al. | |
| 5,397,304 A | 3/1995 | Truckai | |
| 5,656,030 A | 8/1997 | Hunjan et al. | |
| 5,704,898 A | 1/1998 | Kokish | |
| 5,766,196 A * | 6/1998 | Griffiths | ..................... 606/170 |
| 5,820,592 A | 10/1998 | Hammerslag | |
| 5,824,031 A * | 10/1998 | Cookston et al. | ............ 607/122 |
| 5,891,088 A | 4/1999 | Thompson et al. | |
| 5,906,590 A | 5/1999 | Hunjan et al. | |
| 5,954,731 A * | 9/1999 | Yoon | .......................... 606/144 |
| 6,013,052 A | 1/2000 | Durman et al. | |
| 6,126,649 A | 10/2000 | VanTassel et al. | |
| 6,254,568 B1 | 7/2001 | Ponzi | |
| 6,485,455 B1 | 11/2002 | Thompson et al. | |
| 7,008,401 B2 | 3/2006 | Thompson et al. | |
| 7,090,689 B2 * | 8/2006 | Nagase et al. | ................ 606/205 |
| 2003/0125663 A1 | 7/2003 | Coleman et al. | |
| 2005/0107737 A1 * | 5/2005 | McDaniel | ................ 604/95.04 |
| 2005/0245863 A1 | 11/2005 | Coleman et al. | |

FOREIGN PATENT DOCUMENTS

| | | |
|---|---|---|
| DE | 4336040 | 4/1995 |
| EP | 788807 | 6/2003 |
| EP | 787019 | 2/2004 |
| WO | WO 93/20878 | 10/1993 |
| WO | WO 96/34646 | 11/1996 |
| WO | WO 97/42996 | 11/1997 |
| WO | WO 99/53987 | 10/1999 |
| WO | WO 00/67834 | 11/2000 |
| WO | WO 01/68178 | 9/2001 |
| WO | WO 01/89624 | 11/2001 |

* cited by examiner

*Primary Examiner*—Kevin T Truong
(74) *Attorney, Agent, or Firm*—Foley & Lardner LLP (57) ABSTRACT

A medical device is provided with a flexible shaft having a first beam element with a first elongated cross section and a second beam element having a second elongated cross section. An end effector is located at a distal end of the flexible shaft and actuated by relative movement between the first beam element and the second beam element. In another example, a handle is located at a proximate end of the flexible shaft. A first control is mounted on the handle and is directly coupled to the first beam element for placing the first beam element in tension relative to the second beam element to thereby cause bending of at least a portion of the flexible shaft toward the first beam element.

22 Claims, 7 Drawing Sheets

MEDICAL DEVICE USING BEAM CONSTRUCTION AND METHODS

CROSS-REFERENCE TO RELATED PATENT APPLICATIONS

Embodiments of the present invention relate to U.S. Provisional Application Ser. No. 60/747,793, filed May 20, 2006, entitled "Selectively Flexible Surgical Device and Method of Manufacture", the contents of which are incorporated by reference herein and which is a basis for a claim of priority.

FIELD

The present disclosure generally relates to medical devices. The present disclosure relates more specifically to design and construction of medical devices having a flexible shaft.

BACKGROUND

Medical devices, such as surgical tools, developed to cause less patient trauma, can be considered to fall broadly into two classes: 1) rigid instruments, designed to be used through skin incisions under the visual guidance of images obtained through rigid laparoscopes, and 2) miniature, flexible devices designed for use with flexible endoscopes, generally operating through existing bodily orifices.

While the rigid instruments can exert reasonably high operating forces, the very rigidity that enables the operating forces also limits utility because of the need for line of sight access. The miniature, flexible devices are typically limited by the size of working channels in existing endoscopes, and this, coupled with their extreme flexibility, greatly limits the forces they can exert, and thus their utility.

SUMMARY

Various examples of the present invention can provide flexibility to enable maneuverability, while also having properties of increased bending stiffness in some directions. Some of the examples use beams having an elongated cross-section along the length of the flexible portion of the device. Some examples can provide a bending force at a distal end of a flexible shaft, to aid in steering and/or applying a force to a work site, such as by applying a force to one or more beams. Some examples use multiple pieces of material having an elongated cross-section, such as by the use of laminated sheet metal or plastics, providing much of the rigidity of the laparoscopic devices, while also achieving the necessary flexibility to enter the body through natural orifices such as the mouth, nose, anus, urethra and vagina.

One embodiment relates to a medical device having a flexible shaft having a first beam element with a first elongated cross section and a second beam element having a second elongated cross section. An end effector is located at a distal end of the flexible shaft and actuated by relative movement between the first beam element and the second beam element.

A further exemplary embodiment provides a medical device with a flexible shaft having a first beam element having an elongated cross section and a second beam element having an elongated cross section. A handle is located at a proximate end of the flexible shaft. A first control is mounted on the handle and is directly coupled to the first beam element for placing the first beam element in tension relative to the second beam element to thereby cause bending of at least a portion of the flexible shaft toward the first beam element. In this embodiment, the first beam element and second beam element each extend from the handle to a distal end of the flexible shaft.

Another embodiment provides a method of actuating a medical device. The method includes moving a control on a handle. The handle is coupled to a flexible shaft. In response to moving the control, a desired result is provided at a distal end of the flexible shaft by moving, within the handle and the flexible shaft, a first beam element relative to a second beam element. The first beam element and the second beam element each have a ratio between a cross-sectional height dimension and a cross-sectional width dimension of at least 10:1, thereby providing the flexible shaft with a higher bending stiffness in a direction of cross-sectional elongation of the first beam element and second beam element than in a direction perpendicular to the direction of cross-sectional elongation of the first beam element and second beam element. In one example of an implementation of this embodiment, an end effector located at the distal end of the flexible shaft is actuated in response to moving the first beam element relative to the second beam element. In another example of an implementation of this embodiment, the distal end of the flexible shaft moves in a direction perpendicular to the direction of cross-sectional elongation of the first beam element and second beam element when the first beam element is moved relative to the second beam element.

DETAILED DESCRIPTION OF THE EXEMPLARY EMBODIMENTS

Various embodiments of the invention can provide a medical device having a flexible shaft. The flexible shaft can be used with a handle having one or more controls for actuating an end effector for, for example, grasping, holding, cutting, and/or stapling tissue. Example implementations of various embodiments can provide a flexible shaft having a higher bending stiffness along one axis than a bending stiffness in a parallel direction. Such a flexible shaft may be formed by the use of one or more beam elements, the beam elements having an elongated cross-section. Multiple pieces may be used to form each beam element and multiple beam elements may also be used.

Figure 1A:
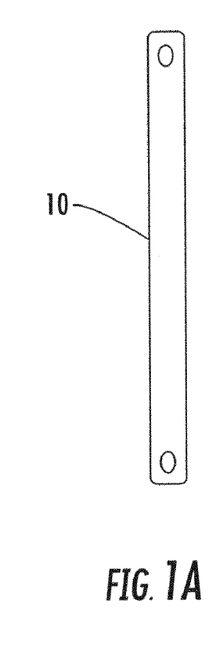
FIG. 1A is a schematic illustration of a beam element according to one exemplary embodiment.
Figure 1B:
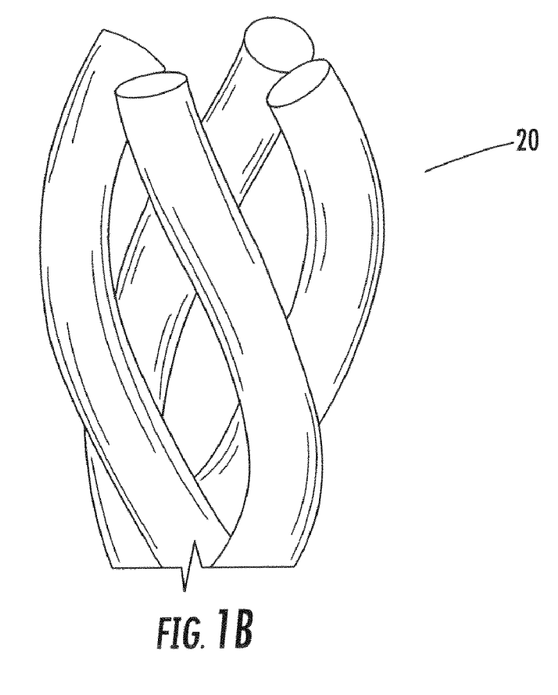
FIG. 1B is a schematic illustration of a stranded cable under a compressive load

With reference to FIGS. 1A and 1B, an example of a beam 10 according to an illustrative embodiment of the invention is shown in FIG. 1A. FIG. 1B illustrates a close-up view of a stranded cable 20. The cable 20 is highly flexible in the XY and XZ planes, while capable of only tensile loads along the length of the cable, i.e. the X axis, perpendicular to the YZ plane. An example of a beam 10 according to an illustrative embodiment of the invention has a higher bending stiffness in the XZ plane, when compared to the bending stiffness in the XY plane. The beam 10 also has greater ability to exert compressive forces along the X axis than a stranded cable 20. As illustrated in FIG. 1B, under compression, the strands of the cable 20 can separate from one another.

The example beam 10 of FIG. 1A provides different level of bending stiffness, as noted above. The geometric (i.e. non-material dependent) term in the stiffness equation is expressed in the form: (b*h3)/12 where b is the width (along the Y axis) of a rectangular prism, and h is the height (along the Z axis). Increasing values of "b" lead to an additive ($A^1$) accretion to the stiffness equation, while increasing "h" causes an exponential ($A^3$) increase in stiffness. This property can be used to make a device highly stiff in one direction, while relatively flexible in another. By contrast, a wire with a square or circular cross section typically has the same stiffness in both directions. Because of the necessary symmetry of wires, (and cables made therefrom) "b" is always equal to "h". The factor reduces as follows: ($b*b^3$)/12 or ($b^4$)/12 adding additional wires (e.g., forming a cable), gives the following: ($b_1^{4} + b_2^{4} + b_3^{4} + b_4^{4} + \ldots + b_n^{4}$)/12 In such a configuration, the stiffness in the XZ plane can only be increased by stiffening the XY plane by the same amount.

In flexible endoscopic and laparoscopic surgery, stiffness is essential during most of the procedure, but mostly undesirable during device insertion and removal. For example, the passage from the mouth into the throat involves primarily a 90 degree bend in a single plane (anatomically, the medial/lateral plane). By inserting the device while the less-stiff XY plane is oriented with the medial lateral plane, a transoral device can successfully negotiate this anatomical feature even if it is highly stiff in the direction NOT being bent. Once inside the body, the stiffness in this direction, when used according to various embodiments of the invention, can be extremely useful in grasping, holding, cutting and/or stapling tissue.

Various embodiments can provide beneficial functionality by the use of different bending stiffnesses in different directions. For example, a grasper—used to manipulate tissue and/or acquire tissue for biopsies, etc.—ideally should be stiff in the plane in which the upper and lower jaws move (Plane XZ). In the perpendicular plane (XY), the device only needs to be stiff enough to avoid buckling under the required functional loads. The third plane, YZ, is the plane around whose axis rotary motion occurs. This motion is often useful for positioning the device relative to the tissue to be acquired. Typically, buckling is avoided by making the device equally stiff in both planes—in other words, far stiffer than necessary.

Various embodiments of the present invention can use one or more materials, such as, for example steel, stainless steel, other metals, or engineering plastics, formed with an elongated cross-section to increase the stiffness in the plane parallel to the elongation, and reduce it significantly in the perpendicular plane. Optionally, stiffening additives such as glass or carbon fibers, may also be used.

The elongated cross section of various embodiments is generally analogous to a cross-section of a 2×4 piece of lumber. In many implementations, a height to width ratio (Y:Z) of at least 10:1 is used, with some implementations having a ratio of 8:1. This ratio may also be 10:1 or greater. Resistance to buckling can be achieved by one or more of the following means: 1) adding a sufficient number of identical (or nearly identical) pieces, e.g. parallel layers; 2) alternating thinner and thicker laminates, and 3) constraining the laminates (whether of the same or different thickness) within a guide tube or overtube either to prevent buckling, or to keep it within acceptable limits. A final, and less desirable, means of limiting buckling is to 4) attach one or more layers together temporarily, as with fasteners, or permanently with welding or adhesives. Joining techniques such as these can cause the properties in the joined region to approximate a solid object. Over small regions, this may be necessary or even desirable, as in the fixation of one end in order that length changes will predictably occur at the other end of the elongate laminate(s). These length changes are due to geometric considerations, in which only the "neutral axis" of a bent member is stress free, with radial segments above and below the neutral axis changing in length due to the magnitude and direction of stresses acting upon them.

Figure 2:
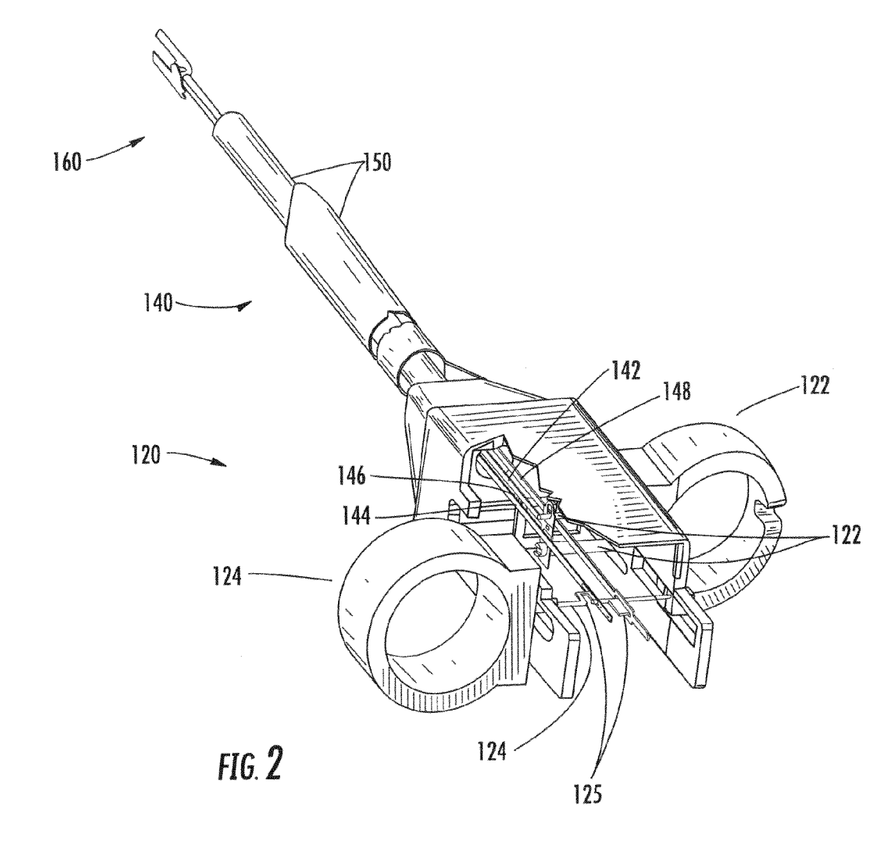
FIG. 2 is a perspective view of a medical device according to an exemplary embodiment.
Figure 3:
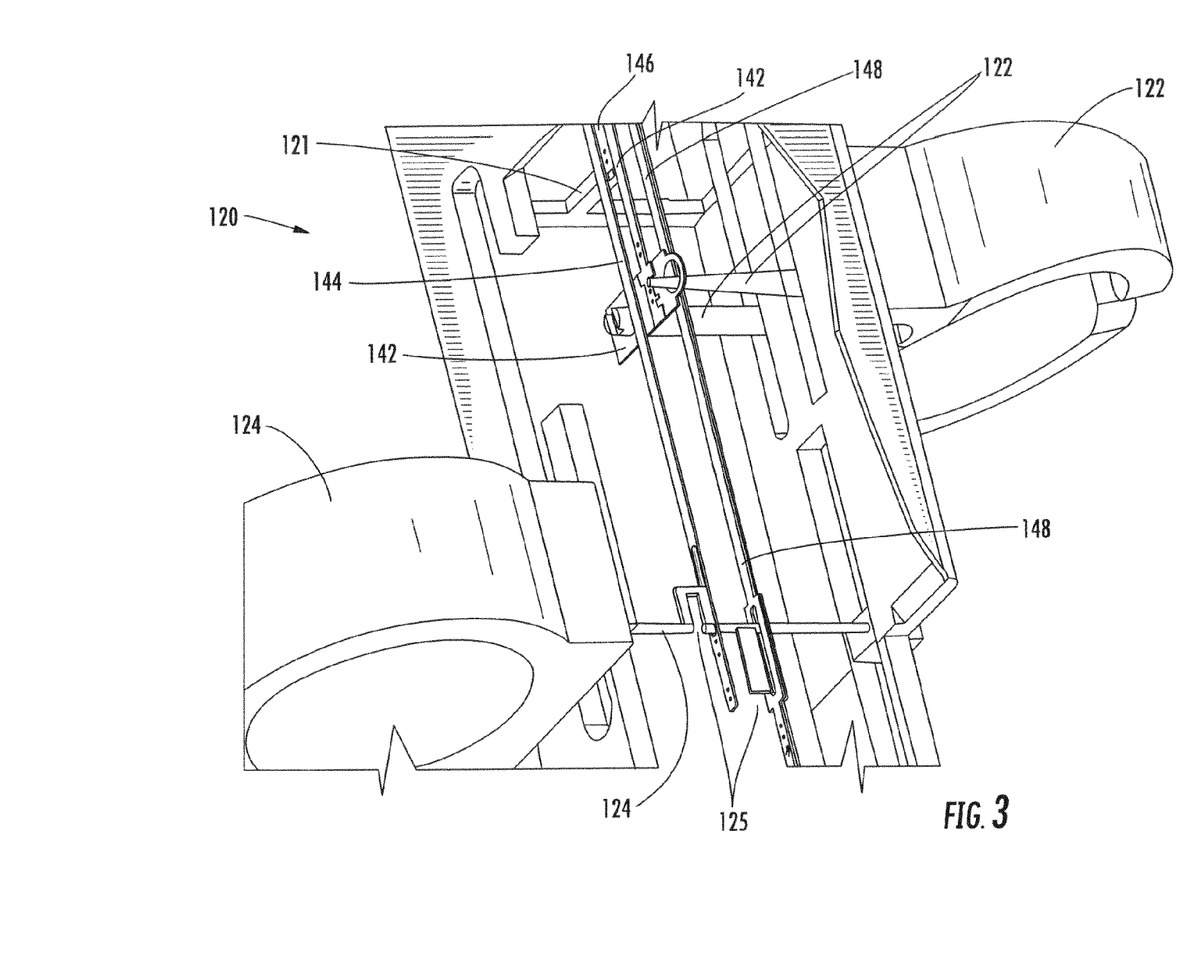
FIG. 3 is a close-up perspective view of the handle of the medical device of FIG. 2 according to an exemplary embodiment.

With reference to FIGS. 2 and 3, a medical device 100 is shown in accordance with an illustrative embodiment of the present invention. The medical device 100 has a handle 120, a flexible shaft 140 and an end effector 160. In the illustrated example, the end effector is a grasper, although other end effectors, such as, for example, a cutter, cutter/stapler, electrode may be used. According to the illustrative embodiment, the medical device 100 is provided with a plurality of beam elements that extend from within the handle 120 to the end effector 160. The flexible shaft 140 can include one or more layers of outer covering 150, such as an outer sheath. The length of the flexible shaft 140 may be maintained by the use of a beam element located therein and/or by the use of a flexible outer covering, permitting bending of the flexible shaft 140, while resistant to compression. Optionally, the outer covering may be retractable or removable, to enable deployment of the medical device into the body, while shielding the end effector from the body cavity through which it is traveling.

One or more controls are mounted to the handle 120 in the example. A first control 122 is directly coupled to a first beam element 142. In the example, the first beam element 142 is configured to actuate the end effector 160, which in the example is opening and closing the grasper. A second control 124 is directly coupled to a second beam element 144. In the example, the second beam element 144 is configured to bend the flexible shaft 140 by application of a force along the second beam element 144. For example, the application of a tensile force on the second beam element 144 can cause a bending of the flexible shaft 140 toward the second beam element 144. In the present example, a third beam element 146 is mounted on a proximal end to the handle 120, such as by the use of an internal structural member 121 of the handle, and at a distal end of the flexible shaft 140, to provide a beam element to resist the tensile force along an offset axis. Such an arrangement can provide a bending motion of the flexible shaft 140 upon application of the tensile force, instead of a collapsing of the flexible shaft by the tensile force from the second beam element 144.

Optionally, a fourth beam element 148 may be provided and directly coupled to the second control 124, or a separate control, to enable the application of a force to an opposite side of the flexible shaft 140. For example, a tensile force may be applied to the fourth beam element 148 by the use of the second control 124.

The second control 124, in the present example, is configured to be moved toward and away from the handle 120 so as to selectively engage the second beam element 144 and fourth beam element 148 so as to be able to apply a tensile force to the second beam element 144 and fourth beam element 148 individually, depending on the desired direction of bending of the flexible shaft 140. The portion of the second control 124 located within the handle 120 is illustrated with offset portions 125 to provide for the above-described selective engagement. It is understood that a wide variety of configurations and geometries may be used to provide for selective engagement. Alternatively or in addition, an additional control may be provided to engage one of the beam elements and cause bending of the flexible shaft 140 in a second direction.

Figure 4:
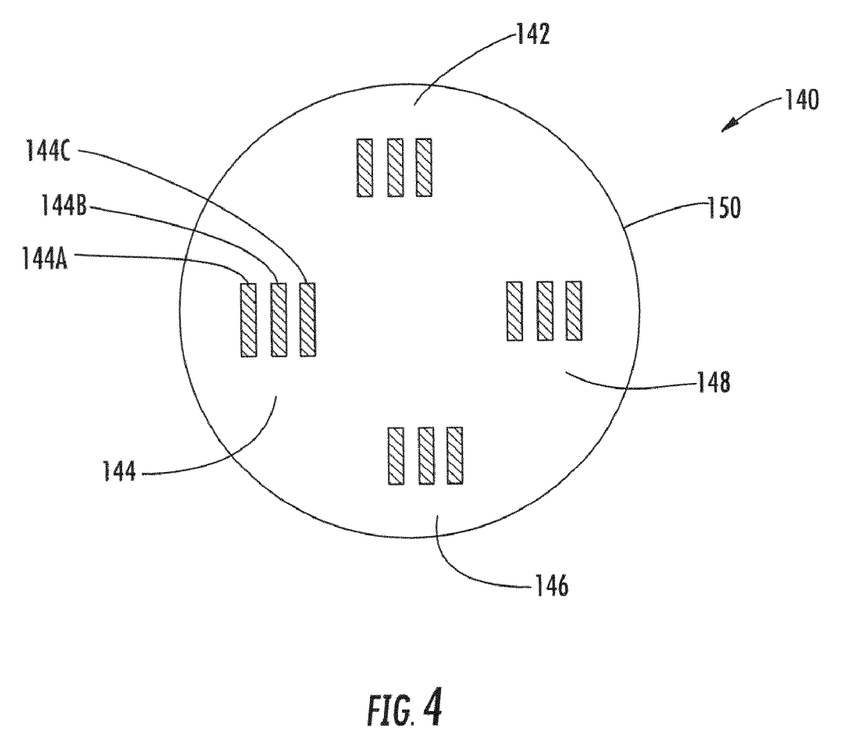
FIG. 4 is a cross-sectional view of the flexible shaft of the medical device of FIG. 2, according to an exemplary embodiment.

FIG. 4 illustrates a cross-sectional view of the flexible shaft 140 having an outer covering 150. A plurality of beam elements 142, 144, 146 and 148 are shown in the lumen of the flexible shaft 140. As shown by way of example, each of the beam elements is formed of multiple pieces. For example, the second beam element 144 is illustrated with three pieces 144A, 144B and 144C. Each of the beam elements may be formed with one, two, three or more pieces forming the beam element. Optionally, each of the pieces are positioned as layers touching neighboring pieces.

Figure 5:
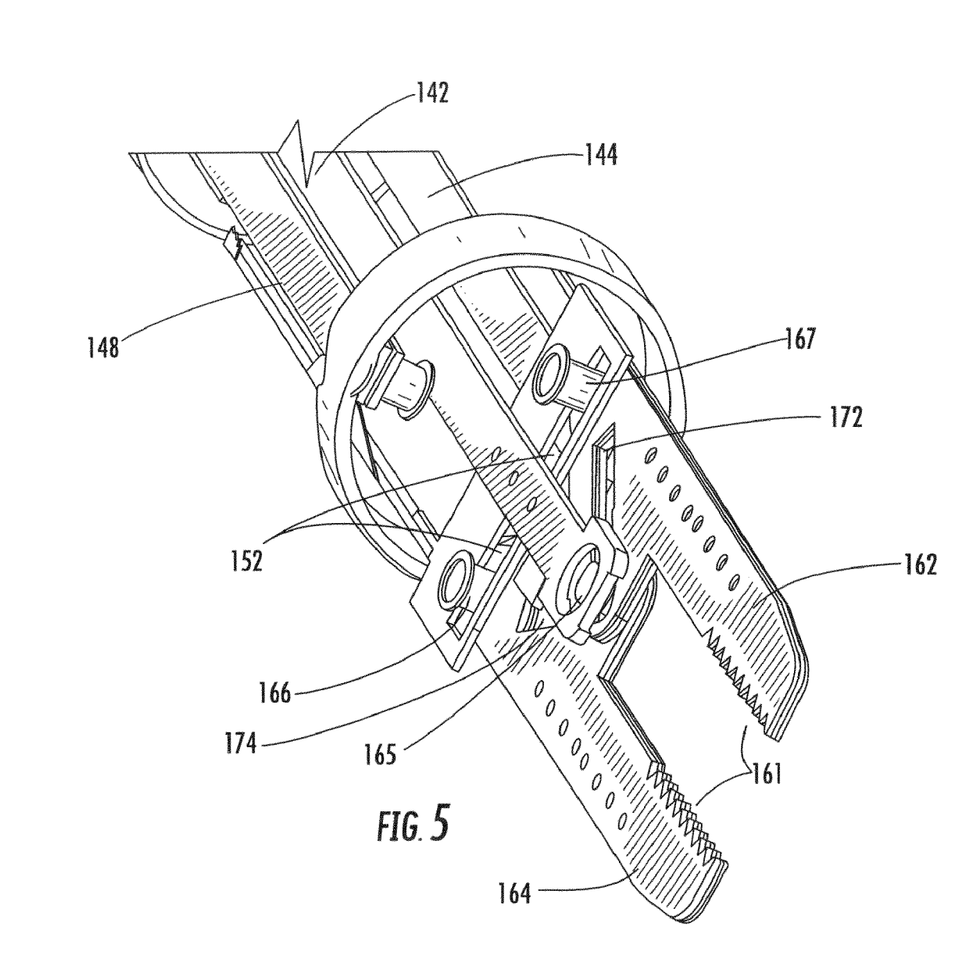
FIGS. 5 and 6 are close-up perspective views of the end effector of the medical device of FIG. 2, according to an exemplary embodiment.
Figure 6:
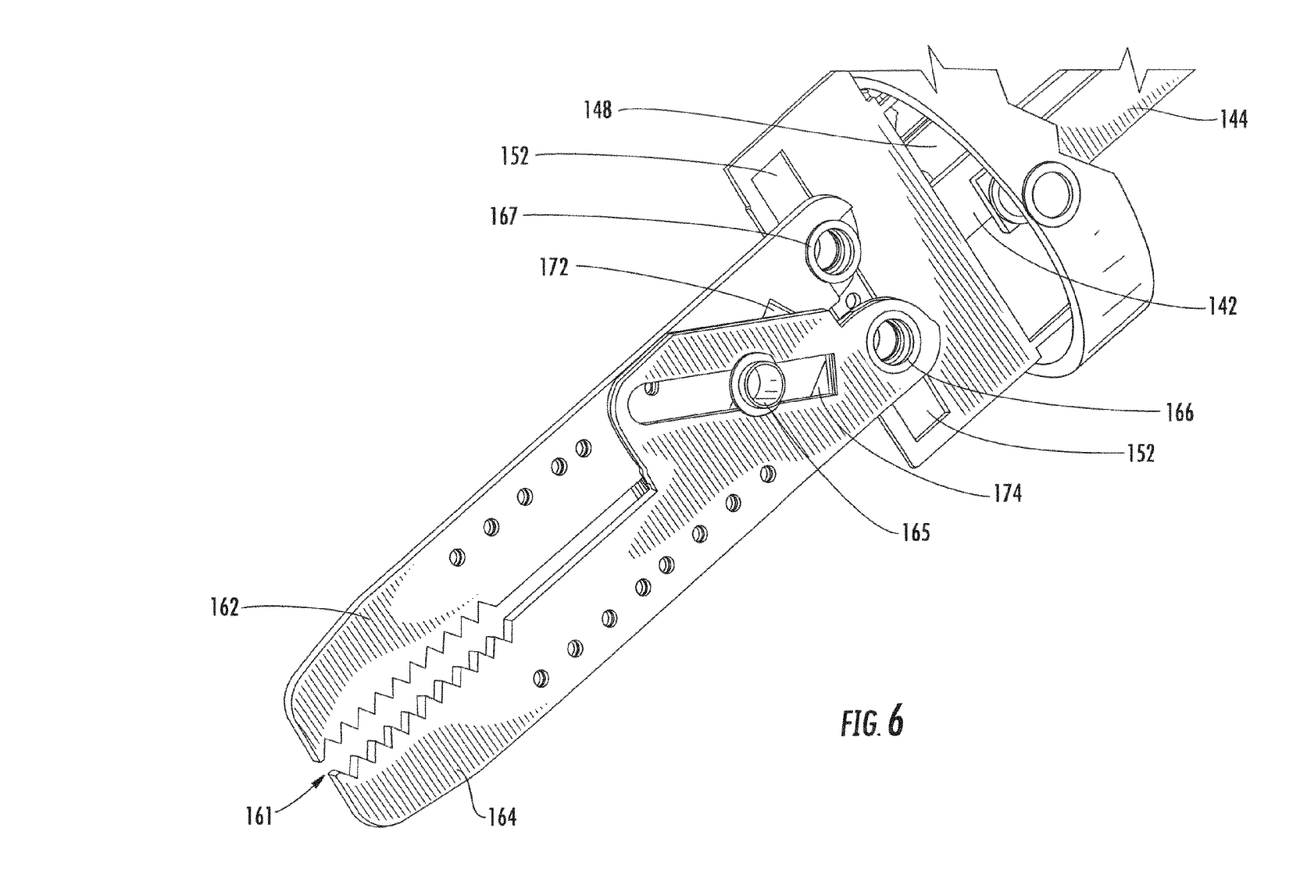

FIGS. 5 and 6 provide perspective views of an end effector 160 in the form of a grasper. The example grasper is formed with a first and second moving jaw 162, 164. FIG. 5 provides a view of the jaws 162, 164 of the grasper in an open position, while FIG. 6 shows the other side of the jaws 162, 164 in an almost-closed position. The jaws 162, 164 move open and closed upon movement of the first beam element 142, thereby moving the closure pin 165 and causing positioning pins 166, 167 to slide laterally. As shown in FIGS. 5 and 6, the closure pin 165 slides within slot 172 of the first jaw 162 and slot 174 of the second jaw 164. The positioning pin 166 is attached to the second jaw 164 and positioning pin 167 is attached to the first jaw 162, with positioning pins 166, 167 configured to slide within slot 152, which is mounted to the flexible shaft 140 and/or a beam element positioning the slot 152 from the handle to resist forces applied by the first beam element 142 through positioning pins 166, 167.

While the jaws 162, 164 of the illustrative embodiment are shown with teeth 161 to enhance grasping, the jaws 162, 164 may be configured with one or more sharp edges to enable cutting.

The jaws 162, 164 are shown as formed of multiple pieces arranged in layers. Such a configuration can optionally provide an ability to have a reduced bending stiffness in a direction perpendicular to the closing direction. Such a configuration can optionally provide enhanced maneuverability over rigid tools having rigidly connected stampings. By replacing the rigid stampings by pieces having an elongated cross-section, such as photoetched or similar parts, many of the functions of a rigid device for laparoscopy may be realized in a device for flexible endoscopy, or for a third or hybrid, that may be described as "flexible laparoscopy". Flexible laparoscopy makes selected elements of a rigid tool into highly function flexible or semi-flexible components by using multi-layer, e.g. laminated, functional or actuating components where appropriate.

Figure 7:
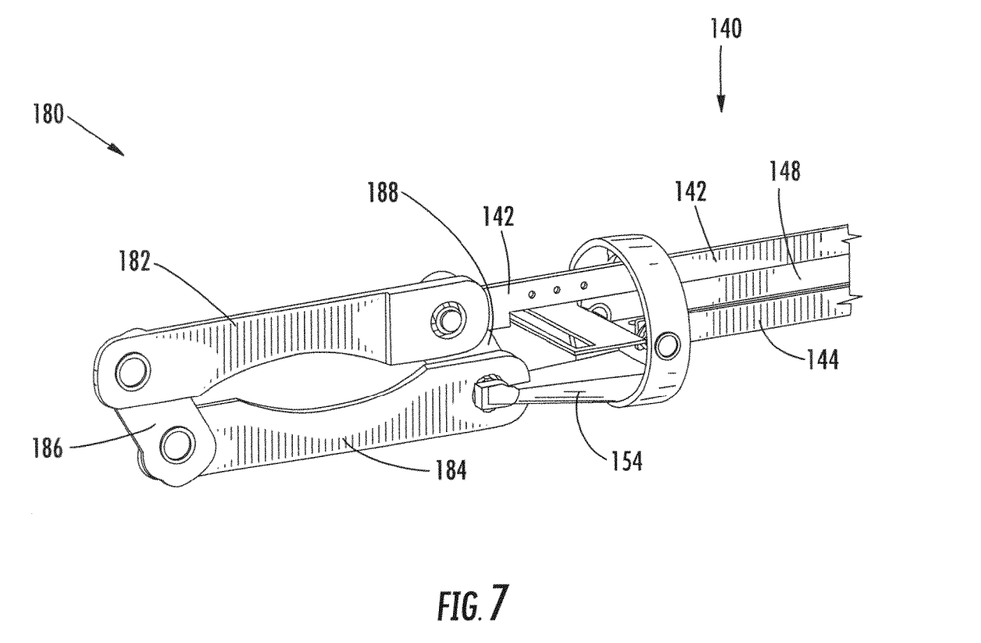
FIG. 7 is a close-up perspective view of an alternative end effector for use with the medical device of FIG. 2, according to another exemplary embodiment.

FIG. 7 provides another example of an end effector 180 in the form of a grasper/cutter. The end effector 180 is illustrated in the form of a four bar linkage. The linkage includes a top bar 182 and a bottom bar 184 that are coupled by two side bars 186, 188. Like the end effector 160 of FIGS. 5 and 6, the end effector 180 of FIG. 7 is actuated by the first beam element 142. Strut 154 may be provided to locate a corner of the linkage relative to the handle, enabling movement of the first beam element 142 to open and close the linkage. The top bar 182 and bottom bar 184 may be configured to grasp, hold and/or cut and item located between them and closed down on by closure of the linkage. The top bar 182 and bottom bar 184 may be formed with an elongated cross-section, thereby providing bending stiffness that varies depending on the direction of bending, allowing the four bar linkage to bend while traveling through the body, but still able to apply adequate closure force, due to a higher bending stiffness in the closure direction.

The end effector 180 of FIG. 7 may be used with other components to simultaneously or sequentially hold, cut and staple tissue during a surgical procedure. Such procedures might include: resection for biopsy, resection as treatment of a cancerous or precancerous lesion, or resection/transection during gastric bypass. The four bar linkage according to the illustrated example has a high ratio (or ratios) of Z to Y in some or all of the top bar 182, bottom bar 184 and/or side bars 186, 188.

Opening and closing of the linkage could occur by any number of means: by the use of properly insulated electric motors within the body, by means of the shape memory effect actuated by heat or electricity, or by mechanical means such as wires, torsion rods, push/pull mechanisms, including those formed of the illustrative example's elongated cross-section bars. Nitinol, available from Nitinol Devices and Components of Fremont, Calif., is an example of a material that can be used for shape memory effect actuated by heat or electricity. The linkage could be held open or closed by continued application of the actuating force, by friction, or by mechanical interlock by any of the aforementioned means.

Stapling and cutting, whether simultaneous or sequential, could be performed. It should be understood that not all of the components need to be formed having an elongated cross-section, but, optionally, only those whose size or other characteristics makes them amenable to improvement in this manner. By way of example, a cutting edge is typically a small member that cannot be made flexible, due to the brittleness inherent in a sharp tool. Nor is it often necessary to make cutting edges flexible, as they can be made very small by only sharpening that portion necessary at the area of tissue contact, and leaving the supporting members to be made preferentially stiff as necessary. The top bar 182 and bottom bar 184 of the linkage may also be designed to be stiff only during the time when a staple or staples are being driven through tissue underneath.

For prototyping and small batch manufacturing, machining from sheet stock and photochemical etching are particularly applicable. Assembly could consist of adding custom and stock springs and/or fasteners, pins and the like, to hold and dispose the various components. For larger volume production, many or all of the components would be stamped or fine blanked from very thin sheet stock. Assembly would be facilitated by the incorporation of locating features, such as dimples, bosses, slots, and piercing, that would orient and/or hold the device components. The stamping process is particularly well suited to the formation of multiple features in a single, complex part, and it is well adapted to the slender, sheet-like substances that are the preferred raw material for the essential components of this invention.

To protect and enclose the components during insertion and use, external coverings might be employed. These could consist of a sheath and/or extruded tubing, for example, made from polyolefin, fluoropolymers, and other plastics. Shrink tubing might also be employed to excellent effect. Alternatively, appropriate coatings or coextrusions could be used, particularly in an effort to reduce internal friction between moving components.

The reusable v. disposable aspect of this invention depends on many factors, particularly the thickness and ruggedness of external and highly stressed components. For the beam elements, great care would be taken to enable the cleaning of contaminated surfaces, perhaps by disassembling the individual layers of any multi-layer construction. In addition, or instead, protective sheaths could prevent the egress of body fluids in the first place. Finally, a disposable sheath over all or part of the device would protect the elements most difficult to clean.

Various embodiments can allow motion in the direction of lesser bending stiffness during insertion of the device into a body cavity, and then to restrain this motion, e.g. increase the bending stiffness, while the device is being used for grasping, cutting, etc. For example, during insertion, a number of laminates may be stacked, parallel, inside a supporting circular tube, with "half moon" shaped spaces on the left and right sides, allowing the device to flex freely from side to side as required by the anatomical curve(s) to be traversed. During use, the "half moon" spaces are less desirable, as this is the space into which the device would move should the applied force be sufficient to induce buckling. Accordingly, this space may be partially or completely filled with a material of appropriate stiffness and frictional characteristics. This could be an elongated strip of material in the "Half moon" shape, or, much more simply, it could be a solid wire (or cable) of appropriate size to restrain most or all of the potential buckling motion. The shape or wire would be inserted after the stiff portion of the device had traversed the tortuous part of the anatomy. Note that this description adds another sort of beneficial asymmetry: the device has a variable stiffness along its length, depending on which components are inside, where they are located along the long axis, and, most importantly, their location relative to the anatomy. This is in contrast to most wire driven devices, which, apart from their extreme proximal and distal portions, have the same stiffness and internal composition along their entire length.

Buckling can be limited, alone or in conjunction with the above, by optionally "banding" the laminates together at regular or other intervals along the length. Thus buckling between one pair of bands would have limited propagation to the next banded segment. The bands are another form of material efficiency: they essentially bear tensile loads only, and thus contribute trivially to bending stiffness during insertion and removal of the device. The band material, and/or its coating, must be chosen to have proper frictional characteristics to allow X-axis motion between adjacent laminates.

Another embodiment provides a method of actuating a medical device. The method includes moving a control on a handle. The handle is coupled to a flexible shaft. In response to moving the control, a desired result is provided at a distal end of the flexible shaft by moving, within the handle and the flexible shaft, a first beam element relative to a second beam element. The first beam element and the second beam element each have a ratio between a cross-sectional height dimension and a cross-sectional width dimension of at least 10:1, thereby providing the flexible shaft with a higher bending stiffness in a direction of cross-sectional elongation of the first beam element and second beam element than in a direction perpendicular to the direction of cross-sectional elongation of the first beam element and second beam element. In one example of an implementation of this embodiment, an end effector located at the distal end of the flexible shaft is actuated in response to moving the first beam element relative to the second beam element. In another example of an implementation of this embodiment, the distal end of the flexible shaft moves in a direction perpendicular to the direction of cross-sectional elongation of the first beam element and second beam element when the first beam element is moved relative to the second beam element.

It is important to note that the construction and arrangement of the present invention as shown in the various exemplary embodiments is illustrative only. Although only a few embodiments of the present inventions have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited in the claims. Accordingly, all such modifications are intended to be included within the scope of the present invention as defined in the appended claims. The order or sequence of any process or method steps may be varied or re-sequenced according to alternative embodiments. Other substitutions, modifications, changes and omissions may be made in the design, operating conditions and arrangement of the exemplary embodiments without departing from the scope of the present inventions as expressed in the appended claims.

What is claimed is:

1. A medical device, comprising:
a flexible shaft comprised of a first beam element having a first elongated cross section and a second beam element having a second elongated cross section, wherein the first and second beam elements are configured to permit relative movement therebetween, and the first and second beam elements are configured to bend the flexible shaft through relative movement between the first and second beam elements caused by application of a force to at least one of the first and second beam elements; and
an end effector, located at a distal end of the flexible shaft and actuated by relative movement between the first beam element and the second beam element.

2. The medical device of claim 1, having a first axis along an elongated dimension of the first elongated cross section and a second axis along an elongated dimension of the second elongated cross section, the first axis being substantially parallel to the second axis.

3. The medical device of claim 2, wherein the flexible shaft has a higher bending stiffness in a direction substantially parallel to the first axis and the second axis than in a direction perpendicular to the first axis and the second axis.

4. The medical device of claim 1, wherein the first beam element and the second beam element each have a rectangular cross section having a ratio between a height dimension and a width dimension of at least 10:1.

5. The medical device of claim 1, wherein the end effector is a grasper.

6. The medical device of claim 1, wherein the end effector comprises a third beam element and a fourth beam element that move relative to each other, and wherein the third beam element and the fourth beam element each have a rectangular cross section having a ratio between a height dimension and a width dimension of at least 10:1.

7. The medical device of claim 6, wherein the third beam element and fourth beam element move relative to each other while coupled by a fifth beam element and sixth beam element in a four bar linkage.

8. The medical device of claim 1, wherein the first beam element and the second beam element are each formed of at least two pieces, each piece having an elongated cross section, the elongated cross sections of each beam element being parallel to each other.

9. The medical device of claim 1, wherein the first beam element and second beam element each extend from the end effector to a handle, the handle located at a proximate end of the flexible shaft.

10. The medical device of claim 1, further comprising:
a third beam element having a third elongated cross section with an elongated dimension substantially parallel to an elongated dimension of the first elongated cross section and an elongated dimension of the second elongated cross section, the third beam element mounted to a distal end of the flexible shaft and extending to a handle; and
a control, located at the handle and coupled to the third beam element for placing the third beam element in tension to bend the distal end of the flexible shaft in the direction of the third beam.

11. The medical device of claim 1, wherein the flexible shaft further comprises an outer sheath.

12. A medical device, comprising:
a flexible shaft comprised of a first beam element having an elongated cross section and a second beam element having an elongated cross section;
a handle, located at a proximate end of the flexible shaft; and
a first control, mounted on the handle, and coupled to the first beam element for placing the first beam element in tension relative to the second beam element to thereby cause bending of at least a portion of the flexible shaft toward the first beam element;
wherein the first beam element and second beam element each extend from the handle to a distal end of the flexible shaft wherein the first and second beam elements are spaced apart from one another.

13. The medical device of claim 12, wherein the first beam element and the second beam element each have a rectangular cross section having a ratio between a height dimension and a width dimension of at least 10:1.

14. The medical device of claim 12, wherein the first beam element and the second beam element are fixedly coupled to each other at the distal end of the flexible shaft.

15. The medical device of claim 12, further comprising:
a third beam element having an elongated cross section and coupled to the distal end of the flexible shaft; and
a second control coupled to the third beam element for placing the third beam element in tension relative to at least one of the first beam element and the second beam element to thereby cause bending of at least a portion of the flexible shaft toward the third beam element.

16. The medical device of claim 15, wherein the first beam element, second beam element and third beam element are each formed of at least three pieces, each piece having an elongated cross section, the elongated dimensions of the elongated cross sections of each beam element being parallel to each other.

17. The medical device of claim 12, further comprising an end effector mounted to the distal end of the flexible shaft.

18. The medical device of claim 17, further comprising:
a third control coupled to a fourth beam element; and
wherein the end effector is a grasper actuated by the third control.

19. A method of actuating a medical device, comprising:
moving a control on a handle, the handle coupled to a flexible shaft; and
in response to the act of moving the control, providing a desired result at a distal end of the flexible shaft by moving, within the handle and the flexible shaft, a first beam element relative to a second beam element, wherein the first and second beam elements are configured to bend the flexible shaft through relative movement between the first and second beam elements caused by application of a force to at least one of the first and second beam elements, wherein the first beam element and the second beam element each have a ratio between a cross-sectional height dimension and a cross-sectional width dimension of at least 10:1, thereby providing the flexible shaft with a higher bending stiffness in a direction of cross-sectional elongation of the first beam element and second beam element than in a direction perpendicular to the direction of cross-sectional elongation of the first beam element and second beam element.

20. The method of claim 19, further comprising, in response to the act of moving the first beam element relative to the second beam element, actuating an end effector located at the distal end of the flexible shaft.

21. The method of claim 19, wherein the act of moving the first beam element relative to the second beam element causes a movement of the distal end of the flexible shaft in a direction perpendicular to the direction of cross-sectional elongation of the first beam element and second beam element.

22. The medical device of claim 12, wherein the first control is directly coupled to the first beam element.

* * * * *